United States Patent
Xu et al.

(10) Patent No.: US 10,690,615 B2
(45) Date of Patent: Jun. 23, 2020

(54) MICRO-NANO TEXTURED GRAPHENE-BASED BIONIC PH SENSOR AND PREPARATION METHOD THEREFOR

(71) Applicant: JIANGSU UNIVERSITY, Jiangsu (CN)

(72) Inventors: Kun Xu, Jiangsu (CN); Xiliang Zhang, Jiangsu (CN); Miaomiao Geng, Jiangsu (CN); Shoujuan Cui, Jiangsu (CN); Pingping Li, Jiangsu (CN); Shiqing Zhang, Jiangsu (CN)

(73) Assignee: JIANGSU UNIVERSITY, Jiangsu (CN)

( * ) Notice: Subject to any disclaimer, the term of this patent is extended or adjusted under 35 U.S.C. 154(b) by 196 days.

(21) Appl. No.: 16/078,038

(22) PCT Filed: May 27, 2016

(86) PCT No.: PCT/CN2016/083578
§ 371 (c)(1),
(2) Date: Aug. 21, 2018

(87) PCT Pub. No.: WO2017/193423
PCT Pub. Date: Nov. 16, 2017

(65) Prior Publication Data
US 2019/0079042 A1    Mar. 14, 2019

(30) Foreign Application Priority Data
May 9, 2016    (CN) .......................... 2016 1 0301183

(51) Int. Cl.
*B82Y 15/00* (2011.01)
*B82Y 5/00* (2011.01)
(Continued)

(52) U.S. Cl.
CPC .............. *G01N 27/302* (2013.01); *B82Y 5/00* (2013.01); *B82Y 15/00* (2013.01); *B82Y 30/00* (2013.01);
(Continued)

(58) Field of Classification Search
CPC ........... B82Y 15/00; B82Y 30/00; B82Y 5/00; G01N 27/302; G01N 27/4146; H01L 51/0048
See application file for complete search history.

(56) References Cited

U.S. PATENT DOCUMENTS

2013/0334579 A1   12/2013   Accardi et al.
2014/0103296 A1    4/2014   Yu et al.

FOREIGN PATENT DOCUMENTS

CN   101236170 A   *   8/2008
CN   101236170 A        8/2008
(Continued)

OTHER PUBLICATIONS

Kuo, L. et al., "A precise pH microsensor using RF-sputtering IrO2 and Ta2O5 films on Pt-electrode," Sensors and Actuators B: Chemical, 2014, 193:687-691.
(Continued)

*Primary Examiner* — Jennifer Wecker
(74) *Attorney, Agent, or Firm* — Saliwanchik, Lloyd & Eisenschenk

(57) ABSTRACT

A micro-nano textured graphene-based bionic pH sensor and a preparation method therefor. The micro-nano textured graphene-based bionic pH sensor comprises a substrate (1), a working electrode (4), a reference electrode (5), a copper contact A (6), a copper contact B (7), an inner lead A (8), and an inner lead B (9). A groove A (2) and a groove B (3) are formed in the substrate (1). The working electrode (4) is located in the groove A (2), and the reference electrode (5)
(Continued)

is located in the groove B (3). The bottom of the working electrode (4) is connected to the inner lead A (8) by means of the copper contact A (6). The top of the reference electrode (5) is connected to the inner lead B (9) by means of the copper contact B (7). The working electrode (4) comprises a graphene group A (401) and a sensitive electrode material layer (402). The sensitive electrode material layer (402) is located on the upper layer of the graphene group A (401). The reference electrode (5) comprises a graphene group B (501) and a metal material silver layer (502). The metal material silver layer (502) is located on the lower layer of the graphene group B (501). Microgrooves or micro pits are formed in the upper surface of the sensitive electrode material layer (402) and the lower surface of the metal material silver layer (502). The pH sensor can fast adsorb water in soil and a culture medium and then adsorb hydrogen ions, and pH in-situ measurement of the soil, the culture medium and other heterogeneous systems is implemented.

9 Claims, 1 Drawing Sheet

(51) Int. Cl.
*G01N 27/30* (2006.01)
*H01L 51/00* (2006.01)
*B82Y 30/00* (2011.01)
*G01N 27/414* (2006.01)
*G01N 27/44* (2006.01)

(52) U.S. Cl.
CPC ..... *G01N 27/4146* (2013.01); *H01L 51/0048* (2013.01)

(56) References Cited

FOREIGN PATENT DOCUMENTS

| CN | 103364463 A | 10/2013 |
|----|-------------|---------|
| CN | 104897755 A | 9/2015 |
| CN | 104914150 A | 9/2015 |

OTHER PUBLICATIONS

Noor, A. M. et al., "A glassy carbon electrode modified with graphene oxide and silver nanoparticles for amperometric determination of hydrogen peroxide," Microchim Acta, Nov. 13, 2015, 183(2):911-916.

Zhang, C. et al., "Microwave assisted one-pot synthesis of graphene quantum dots as highly sensitive fluorescent probes for detection of iron ions and pH value," Talanta, 2016, 150:54-60.

Zuliani, C. et al., "A potentiometric disposable sensor strip for measuring pH in saliva," Electrochimica Acta, 2014, http://dx.doi.org/doi:10.1016/j.electacta.2014.03.140.

* cited by examiner

MICRO-NANO TEXTURED GRAPHENE-BASED BIONIC PH SENSOR AND PREPARATION METHOD THEREFOR

CROSS REFERENCE TO RELATED APPLICATIONS

This application is a National Stage Application of International Application Number PCT/CN2016/083578, filed May 27, 2016; which claims priority to Chinese Application No. 201610301183.X, filed May 9, 2016.

I. TECHNICAL FIELD

The presented invention belongs to the domain of chemical sensor fabrication. The invention relates to a new biomimetic graphene-based pH sensor with micro/nano texturing surface and its fabrication, which is used for pH in-situ measurement in heterogeneous environments such as soil or cultivation substrate with certain moisture content, and pH measurement in solution.

II. BACKGROUND ART

Soil and cultivation substrate are mixed component of mineral and organic matter, which exist solid, gas, and liquid states and belong to heterogeneous environment. Liquids and gases are mainly existed in the gap between solid particles. The complex composition and heterogeneous mixture environments lead totally different physical and chemical properties of the soil, which make it difficult to measure the physical and chemical properties of the soil and cultivation substrate in-situ.

It is essential to detect the concentration of hydrogen ions during pH measurement of soils and cultivation substrates. The hydrogen ions are mainly produced by acid ionization in water. Hydrogen ions are "naked" protons with tiny radius, which turn into hydronium ions ($H_3O^+$) through combined with other water molecules easily. Hydrogen ions exist in the form of hydronium ions usually. Therefore, the hydrogen ions in the soil are closely related to the water in the soil. To realize the in-situ measurement of the pH of heterogeneous systems such as soil substrates, it is necessary to find a way to quickly absorb the water in the soil. Then hydrogen ions are adsorbed, and the pH of soil culture substrate can be measured in-situ quickly.

The research of existing pH sensor mainly focused on electrode materials, electrode modification methods and composite electrode preparation. Li-Min Kuo prepared a novel pH microsensor in his paper "A precise pH microsensor using RF-sputtering IrO2 and Ta2O5 films on Pt-electrode" which used Ta2O5 to modify the surface of IrO2 electrode by magnetron sputtering technology. In the paper of "A potentiometric disposable sensor strip for measuring pH in saliva", Claudio Zuliani used screen printing technology to print a solid-state reference electrode and ion sol reference electrode on a printed electrode substrate, then formed an all-solid-state complex pH electrode for rapid detection of pH in oral saliva. These studies extended the use of pH electrode to a certain extent and effectively improved the response performance of pH electrodes, such as sensitivity, stability and anti-interference. However, there is no effective solution for pH in-situ measurement in heterogeneous systems and how to allow the electrodes to adsorb water in the soil and cultivate substrates rapidly, and then absorb the hydrogen ions.

III. CONTENTS OF THE INVENTION

In the prior art, the pH in-situ measurement of heterogeneous environments, such as soils and cultivation substrates cannot be solved. This invention provided a new biomimetic graphene-based pH sensor with micro/nano texturing surface and its fabrication, which allows the electrodes to adsorb water in soil and cultivate substrates rapidly and absorb the hydrogen ions, realizing the pH in-situ measurement of heterogeneous environments such as soils and cultivation substrates.

The present invention achieves/realizes the above technical purposes through the following technical methods.

A micro-nano-textured graphene-based biomimetic pH sensor consists of substrate, slot A, slot B, working electrode, reference electrode, copper contact A, copper contact B, inner lead A, and inner lead B. The upper and lower surfaces of the substrate are respectively provided with a slot A and a slot B. The working electrode and reference electrode are located in the slot A and slot B respectively. The bottom of working electrode is connected with the inner lead A through the copper contact A, while the top of reference electrode is connected to the inner lead B through the copper contact B. The working electrode includes graphene A and sensitive electrode material layer and the sensitive electrode material layer is located on the upper layer of the graphene A. The reference electrode includes graphene B and silver metal material layer and the silver metal material layer is located below the graphene B. The upper surface of sensitive electrode material layer and the lower surface of silver metal material layer are both provided with micro-grooves or micro-pits.

Preferably, the micro-grooves or micro-pits are nano-sized and the apparent contact angle is less than 5°.

Preferably, the sensitive electrode material layer is one kind of main-group metal or main-group metal oxide.

Preferably, the sensitive electrode material layer is one of main-group metal, such as Ru, Ir, Pd, Sb, Ti, Ta and Sn, or the corresponding metal oxide.

The fabrication method of the biomimetic graphene-based pH sensor with micro/nano texturing surface is described below:

S1. Slotting on the two sides of the substrate to prepare slot A and slot B, then setting the copper contact A and copper contact B on the bottom of slot A and slot B, and connecting with the inner lead A and inner lead B respectively.

S2. Graphene A is deposited on the upper surface of copper contact A and slot A, while graphene B is deposited on the upper surface of copper contact B and slot B. Coating the sensitive electrode material layer on the upper surface of graphene A and processing micro-grooves or micro-pits on the surface of the sensitive electrode material layer to prepare the working electrode.

S3. Depositing the silver metal material layer on the lower surface of the graphene B and processing micro-grooves or micro-pits on the surface of silver metal material layer. Then chlorinating the lower surface of the silver metal material layer with FeCl$_3$ solution. The graphene powder is dispersed in deionized water and dispersed by ultrasound to prepare the graphene oxide modified film, which is dripped on the lower surface of the silver metal material layer through pipette and dried at room temperature to prepare the reference electrode. Then the biomimetic graphene-based pH sensor with micro/nano texturing surface is prepared.

Preferably, in step S2, the fabrication method of graphene film is micro mechanical peeling transfer method and the thickness of the graphene film is 5~10 nm.

Preferably, the fabrication method of sensitive electrode material layer in step S2 and silver metal material layer in step S3 can be electrochemical deposition, physical vapor deposition or chemical vapor deposition.

Preferably, the method of processing micro-grooves or micro-pits in step S2 and S3 can be femtosecond laser processing, plasma etching, electrochemical etching or acid-base corrosion.

Preferably, the preparation method of the graphene oxide modified film in step S3 is sol-gel method, and the thickness of the graphene oxide modified film is 10-20 nm.

By means of this fabrication method, the performance of the pH sensor will be improved in many indexes.

(1) In the fabrication method of biomimetic graphene-based pH sensor with micro/nano texturing surface, the textured groove or pit structure is prepared on the surface of sensitive electrode material layer and silver metal material layer, which exhibits superhydrophilicity and can absorb the hydrogen ions in soils and cultivation substrates with certain moisture content quickly. For pH measurement of soils and cultivation substrates, it is essential to measure the concentration of hydrogen ions in the soils and cultivation substrates. Therefore, this pH sensor can realize rapid measurement and reduce reaction time. Meanwhile, nano-scale ultra-hydrophilic texture surface possesses self-cleaning biomimetic effect.

(2) In the present invention, graphene is used as substrate material to increase the conductivity and make the response time further reduce. In the preparation of reference electrode, graphite oxide is used as a surface modification to isolate the external interference and achieve the purpose of electron conduction.

(3) In the present invention, the working electrode and reference electrode are placed in the groove of the substrate to reduce the wear of the pH sensor and increase its service life.

IV. DESCRIPTION OF DRAWINGS

Figure 1:
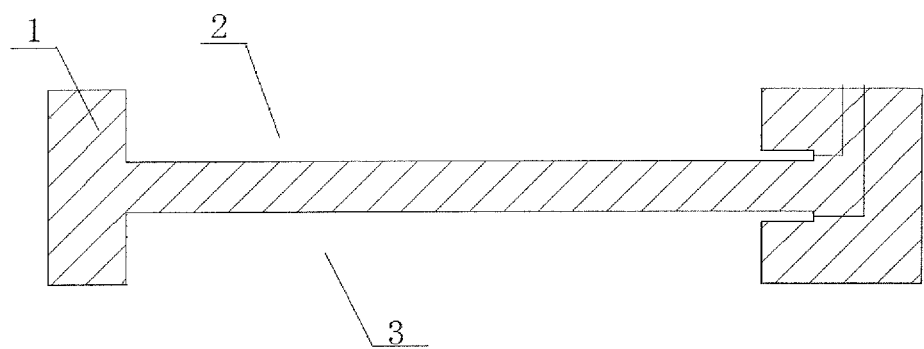
FIG. 1 is a structure of the pH sensor substrate.
Figure 2:
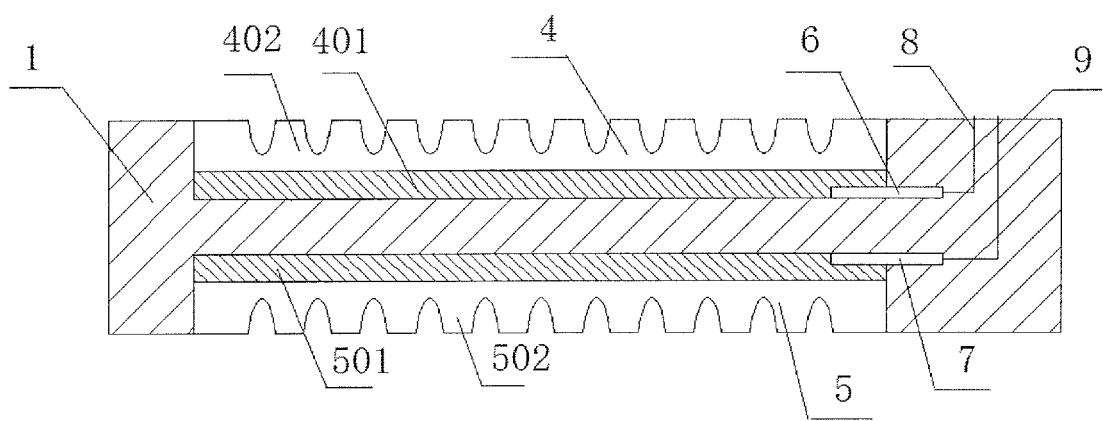
FIG. 2 is a schematic of the biomimetic graphene-based pH sensor with micro/nano texturing surface.

In these FIGURES, 1 is the substrate, 2 is the slot A, 3 is the slot B, 4 is the working electrode, 5 is the reference electrode, 6 is the copper contact A, 7 is the copper contact B, 8 is the inner lead A, 9 is the inner lead B, 401 is the graphene A, 402 is the sensitive electrode material layer, 501 is the graphene B, 502 is the silver metal material layer.

V. EMBODIMENTS

Further description of this invention is presented combined with the drawing, but the protection scope of this invention is not limited to this disclosed description.

Embodiment 1

S1. Slotting on the two sides of the substrate 1 to prepare slot A 2 and slot B 3. Then setting the copper contact A 6 and copper contact B 7 on the bottom of slot A 2 and slot B 3, and connected with the inner lead A 8 and inner lead B 9 respectively.

S2. Through the method of micro mechanical peeling transfer, graphene A 401 is deposited on the upper surface of copper contact A 6 and slot A 2 by graphene film whose thickness is 5 nm, while graphene B 501 is deposited on the upper surface of copper contact B 7 and slot B 3. Antimony is used to prepare the sensitive electrode material layer 402 on the upper surface of graphene A 401 by magnetron sputtering method, the vacuum is $3 \times 10^{-4}$ Pa, the process pressure is 1 Pa, the power is 50 W, the shielding gas is argon, the flow is 39 sccm, and the time is 40 min. Using femtosecond laser processing equipment to process micro-pits on the surface of the sensitive electrode material layer 402, the hole depth is ~80 nm, the hole diameter is ~2 μm. Then the working electrode 4 is prepared.

S3. Depositing the silver metal material layer 502 on the lower surface of the graphene B 501 by magnetron sputtering method, the sputtering is completed at room temperature, the vacuum is $3 \times 10^{-4}$ Pa, the process pressure is 1 Pa, the power is 20 W, the shielding gas is argon, the flow is 30 sccm, and the time is 30 min. The micro-pits whose depth is ~80 nm and diameter is ~2 μm is processed on the surface of ruthenium oxide layer with femtosecond laser processing equipment Then chlorinating the lower surface of the silver metal material layer 502 with $FeCl_3$ solution to produce silver chloride particles on the surface, the concentration of the used ferric chloride solution is 0.05 mol/L, and the soak time is 30 s. Dispersing graphene powder was in deionized water and ultrasonic for 1 h to prepare the graphene oxide modified film with the thickness of 10 nm. Dripping 50 μL graphene oxide on the lower surface of the silver metal material layer 502 by pipette and drying at room temperature to prepare the reference electrode 5. Then the biomimetic graphene-based pH sensor with micro/nano texturing surface is prepared.

Embodiment 2

S1. Slotting on the two sides of the substrate 1 to prepare groove A 2 and slot B 3. Then setting the copper contact A 6 and copper contact B 7 on the bottom of slot A 2 and slot B 3, and connected with the inner lead A 8 and inner lead B 9 respectively.

S2. Through the method of micro mechanical peeling transfer, graphene A 401 is deposited on the upper surface of copper contact A 6 and slot A 2 by graphene film whose thickness is 10 nm, while graphene B 501 is deposited on the upper surface of copper contact B 7 and slot B 3. Ruthenium oxide is used to prepare the sensitive electrode material layer 402 on the upper surface of graphene A 401 by magnetron sputtering method. The sputtering is completed at room temperature, the vacuum is $3 \times 10^{-4}$ Pa, the process pressure is 1 Pa, the power is 100 W, the concentration ratio of argon and oxygen is 9:1, the flow is 45 sccm, and the time is 90 min. The micro-pits whose depth is ~80 nm and diameter is ~2 μm is processed on the surface of ruthenium oxide layer with femtosecond laser processing equipment. Then the working electrode 4 is prepared.

S3. Depositing the silver metal material layer 502 on the lower surface of the graphene B 501 by magnetron sputtering method, the sputtering is completed at room temperature, the vacuum is $3(10^{-4}$ Pa, the process pressure is 1 Pa, the power is 20 W, the shielding gas is argon, the flow is 30 sccm, and the time is 30 min. Using femtosecond laser processing equipment to process micro-pits on the surface of the silver metal material layer 502, the hole depth is ~80 nm, the hole diameter is ~2 μm. Then chlorinating the lower surface of the silver metal material layer 502 with $FeCl_3$ solution to produce silver chloride particles on the surface, the concentration of the used ferric chloride solution is 0.05 mol/L, and the soak time is 30 s. The graphene oxide modified film with the thickness of 20 nm is prepared by dispersing graphene powder in deionized water and ultrasonic dispersing for 1 h. Dripping 50 μL graphene oxide on the lower surface of the silver metal material layer 502 by pipette and drying at room temperature, reference electrode 5 is prepared. Then the biomimetic graphene-based pH sensor with micro/nano texturing surface is prepared.

The two preferred embodiments is the optimal implementation scheme, but this invention is not limited to this disclosed implementation scheme. The protection scope of this invention includes any obvious improvements, replaces or variations by technical staff of this area.

The invention claimed is:

1. A biomimetic graphene-based pH sensor with micro/nano texturing surface, wherein, the pH sensor consists of substrate, slot A, slot B, working electrode, reference electrode, copper contact A, copper contact B, inner lead A, and inner lead B; the upper and lower surfaces of the substrate are respectively provided with a slot A and a slot B; the working electrode and reference electrode are located in the slot A and slot B respectively; the bottom of the working electrode is connected with the inner lead A through the copper contact A, while the top of the reference electrode is connected with the inner lead B through the copper contact B; the working electrode includes graphene A and sensitive electrode material layer; the sensitive electrode material layer is located on the upper layer of the graphene A; the reference electrode includes graphene B and silver metal material layer; the silver metal material layer is located below the graphene B; the upper surface of sensitive electrode material layer and the lower surface of silver metal material layer are both provided with micro-grooves or micro-pits.

2. The biomimetic graphene-based pH sensor with micro/nano texturing surface according to claim 1, wherein, the micro-grooves or micro-pits are nano-sized and the apparent contact angle is less than 5°.

3. The biomimetic graphene-based pH sensor with micro/nano texturing surface according to claim 1, wherein, the sensitive electrode material layer is a main-group metal or main-group metal oxide.

4. The biomimetic graphene-based pH sensor with micro/nano texturing surface according to claim 3, wherein, the sensitive electrode material layer is selected from Ru, Ir, Pd, Sb, Ti, Ta and Sn, or the corresponding metal oxide.

5. A fabrication method for producing a biomimetic graphene-based pH sensor with micro/nano texturing surface according to claim 3, which comprises the steps of:

S1: slotting on the two sides of the substrate to prepare slot A and slot B, then setting the copper contact A and copper contact B on the bottom of slot A and slot B, and connected with the inner lead A and inner lead B respectively;

S2: graphene A is deposited on the upper surface of copper contact A and slot A, while graphene B is deposited on the upper surface of copper contact B and slot B; coating the sensitive electrode material layer on the upper surface of graphene A, then processing micro-grooves or micro-pits on the surface of the sensitive electrode material layer to prepare the working electrode; and S3: depositing the silver metal material layer on the lower surface of the graphene B and processing micro-grooves or micro-pits on the surface of silver metal material layer; then chlorinating the lower surface of the silver metal material layer with $FeCl_3$ solution; the graphene powder was dispersed in deionized water, and then was dispersed by ultrasound to prepare the graphene oxide modified film, which was dripped on the lower surface of the silver metal material layer through pipette; dried at room temperature to prepare the reference electrode; then the biomimetic graphene-based pH sensor with micro/nano texturing surface is prepared.

6. The fabrication method of a biomimetic graphene-based pH sensor with micro/nano texturing surface according to claim 5, wherein, in step S2, the fabrication method of graphene film is micro mechanical peeling transfer method and the thickness of the graphene film is 5~10 nm.

7. The fabrication method of a biomimetic graphene-based pH sensor with micro/nano texturing surface according to claim 5, wherein, the fabrication method of sensitive electrode material layer in step S2 and silver metal material layer in step S3 can be electrochemical deposition or physical vapor deposition, or chemical vapor deposition.

8. The fabrication method of a biomimetic graphene-based pH sensor with micro/nano texturing surface according to claim 5 wherein, the method of processing micro-grooves or micro-pits in step S2 and S3 is femtosecond laser processing, plasma etching, electrochemical etching, or acid-base corrosion.

9. The fabrication method of a biomimetic graphene-based pH sensor with micro/nano texturing surface according to claim 5, wherein the preparation method of the graphene oxide modified film in step S3 is sol-gel method, and the thickness of the graphene oxide modified film is 10-20 nm.

* * * * *